US012746204B2

(12) United States Patent
Stabler et al.

(10) Patent No.: US 12,746,204 B2
(45) Date of Patent: Sep. 29, 2026

(54) MODULAR, OXYGEN-GENERATING MICROBEAD MATERIALS FOR SUPPORTING CELL VIABILITY AND FUNCTION

(71) Applicant: University of Florida Research Foundation, Inc., Gainesville, FL (US)

(72) Inventors: Cherie Stabler, Gainesville, FL (US); Jiapu Liang, Gainesville, FL (US); Robert P. Accolla, Gainesville, FL (US)

(73) Assignee: University of Florida Research Foundation, INC., Gainesville, FL (US)

( * ) Notice: Subject to any disclaimer, the term of this patent is extended or adjusted under 35 U.S.C. 154(b) by 1102 days.

(21) Appl. No.: 17/770,061

(22) PCT Filed: Nov. 6, 2020

(86) PCT No.: PCT/US2020/059264
§ 371 (c)(1),
(2) Date: Apr. 19, 2022

(87) PCT Pub. No.: WO2021/101728
PCT Pub. Date: May 27, 2021

(65) Prior Publication Data

US 2022/0395463 A1 Dec. 15, 2022

Related U.S. Application Data

(60) Provisional application No. 63/071,742, filed on Aug. 28, 2020, provisional application No. 62/936,907, filed on Nov. 18, 2019.

(51) Int. Cl.
*A61K 9/16* (2006.01)
*A61K 9/00* (2006.01)

(52) U.S. Cl.
CPC .......... *A61K 9/1682* (2013.01); *A61K 9/0019* (2013.01)

(58) Field of Classification Search
CPC ... A61K 9/1682; A61K 9/0019; A23L 29/206; A23L 33/135; A23L 11/30
See application file for complete search history.

(56) References Cited

U.S. PATENT DOCUMENTS

2005/0177118 A1* 8/2005 Hoganson .............. A61K 38/15 623/1.42
2009/0205829 A1 8/2009 Sullivan et al.
2012/0114729 A1* 5/2012 Stabler .................... A61L 27/54 435/375
2021/0113736 A1* 4/2021 Camci-Unal ........... A61L 27/54

FOREIGN PATENT DOCUMENTS

CN 110171865 A 8/2019
KR 101361486 B1 2/2014
KR 20190017137 A 2/2019
WO 2019126169 A1 6/2019

OTHER PUBLICATIONS

ISR mailed Feb. 2, 2021, pp. 1-12.

* cited by examiner

*Primary Examiner* — Monica A Shin
(74) *Attorney, Agent, or Firm* — Thomas | Horstemeyer LLP.

(57) ABSTRACT

The present disclosure provides for spherical microbeads, methods of making, and methods of use. The spherical microbeads can be tailored to deliver one or more agents over a desired time frame (e.g., short burst or extended-release or combinations thereof). For example, spherical microbeads can be used for the extended-release of oxygen. The spherical microbeads are amendable for an injectable approach and/or ease of integration within cellular implants due in part to their spherical dimensions and size.

21 Claims, 6 Drawing Sheets

MODULAR, OXYGEN-GENERATING MICROBEAD MATERIALS FOR SUPPORTING CELL VIABILITY AND FUNCTION

CROSS-REFERENCE TO RELATED APPLICATIONS

This application is the 35 U.S.C. § 371 national stage of PCT application having serial number PCT/US2020/059264, filed on Nov. 18, 2020. PCT/US2020/059264 claims priority to U.S. provisional application entitled "MODULAR, OXYGEN-GENERATING MICROBEAD MATERIALS FOR SUPPORTING CELL VIABILITY AND FUNCTION" having Ser. No. 63/936,907 filed on Nov. 18, 2019. In addition, PCT/US2020/059264 also claims the benefit of and priority to U.S. Provisional Application Ser. No. 63/071,742, filed on Aug. 28, 2020, which are entirely incorporated herein by reference.

FEDERAL SPONSORSHIP

This invention was made with government support under Grant No. 3-SRA-2015-38-Q-R, awarded by the Juvenile Diabetes Research Foundation. The government has certain rights in the invention.

NON-FEDERAL FUNDING

This invention was made in part or in whole with support under Grant No. 3-SRA-2015-38-Q-R, awarded by the Juvenile Diabetes Research Foundation.

BACKGROUND

While native tissues are richly vascularized, the implantation of cells or engineered tissues commonly suffer from inadequate oxygenation due to lack of this vascular network. Hypoxia is a serious issue arising within cell-based implants larger than 200 μm that do not permit intra-device vascularization, such as macroencapsulation or immunoisolatory platforms. Mitigating hypoxia-induced cell death and dysfunction should significantly improve the efficacy of those implants, particularly for cells highly sensitive to hypoxia, such as pancreatic beta cells. In situ oxygen generation provides a promising approach for this cause, but current technologies suffer from various deficiencies such as strict geometrical constraints, lack of injectability, insufficiently controlled or durable release profiles, and the like.

SUMMARY

Embodiments of the present disclosure provide for spherical microbeads, methods of making, and methods of use. The present disclosure provides for an embodiment that includes a composition comprising: a plurality of spherical microbeads having the characteristic for extended release of oxygen for a first time frame, wherein the microbead has an average particle diameter of about 100 to 1000 μm, wherein the microbeads have a hydrophobic polymeric support structure containing solid oxygen-generating peroxide particles in an amount sufficient for extended release of oxygen. The time frame for release can be for about 1 week or more, about 30 days or more, optionally the microbeads each have the characteristic of extended release of oxygen at levels of $1\times10^{-6}$ mmol of oxygen per day or more for about 30 days or more. The hydrophobic polymeric support structure can be made of a material selected from: organosilicones, poly(ethersulfone), poly(ethylene oxide terephthalate) block copolymers, polysulfone, and combinations thereof and the solid oxygen-generating peroxide particles can be a $CaO_2$ particle.

The present disclosure provides for an embodiment that includes a composition comprising: a plurality of spherical microbeads, wherein the microbead has an average particle diameter of about 100 to 1000 μm, wherein the microbeads have a hydrophobic polymeric support structure containing solid oxygen-generating peroxide particles in an amount sufficient for extended release of oxygen, wherein the microbeads each have the characteristic of extended release of oxygen at levels of $1\times10^{-6}$ mmol of oxygen per day or more for about 30 days or more. The microbeads can include porogens within the microbead, wherein the porogens are selected from salt, glucose, or hydrogels or a combination thereof, wherein the microbeads have a therapeutic agent within the pores, and wherein the microbead each have the characteristic of extended release of the therapeutic agent for about 30 days or more.

The present disclosure provides for an embodiment that includes a composition comprising: a plurality of spherical microbeads having the characteristic for extended release of oxygen for a first time frame, wherein the microbead has an average particle diameter of about 100 to 1000 μm, wherein the microbeads have a hydrophobic polymeric support structure containing solid oxygen-generating peroxide particles in an amount sufficient for extended release of oxygen, wherein the microbeads have an outer layer that is made of a material selected from: organosilicones, poly(ethersulfone), poly(ethylene oxide terephthalate) block copolymers, polysulfone, and combinations thereof, the wherein outer layer has a thickness of about 11 to 25 μm, and wherein the outer layer includes a therapeutic agent, a solid oxygen-generating peroxide particle, or a combination thereof. The microbeads can have porogens within the microbead, wherein the porogens are selected from salt, glucose, or hydrogels or a combination thereof, wherein the microbeads have a therapeutic agent within the pores. The microbead can each have the characteristic of extended release of the therapeutic agent for about 3 days or more or 30 days or more.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1A:
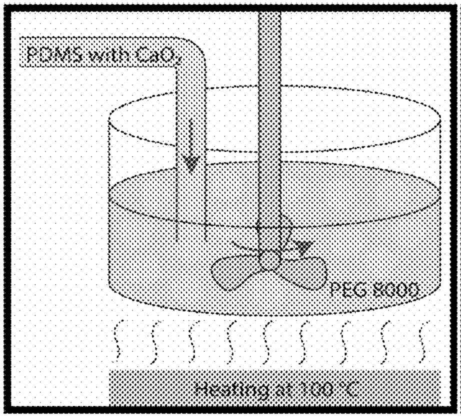
FIGS. 1A-1B illustrates a schematic of microbead fabrication and layering.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, is to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of inorganic chemistry, materials science, nanotechnology and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of chemistry, materials science, medicine, and/or nanotechnology. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for spherical microbeads, methods of making, and methods of use. Spherical microbeads of the present disclosure can be tailored to deliver one or more agents over a desired time frame (e.g., short burst or extended-release or combinations thereof). For example, spherical microbeads of the present disclosure can be used for the extended-release of oxygen. The spherical microbeads are amendable for an injectable approach and/or ease of integration within cellular implants due in part to their spherical dimensions and size. In an aspect, the spherical microbeads provide for a customizable oxygen generating material that easily integrates into any cellular transplant to minimize hypoxia-induced cell death by locally delivering the appropriate amount of oxygen to the cells over a desired time frame (e.g., on the order of day or 30 days or longer), while also providing the option to simultaneously deliver other therapeutic agents over the desired time frame. The flexibility and options for delivering multiple agents allow the spherical microbeads to be used as a microbead platform or for integration into a 3D scaffold.

Microbeads for delivering dynamic, extended-release of oxygen is disclosed. The microbead diameter can range from 100 to 1000 μm. The geometrical shape is predominantly (e.g., about 95-100%) or substantially spherical (e.g., about 80 to 95%). The composition can include a hydrophobic polymeric support structure and optional outer layers of polymeric material. The hydrophobic polymeric support structure can contain one or more types of agents, such as solid oxygen-generating peroxide particles or soluble therapeutic agents. With this design, the microbeads can be tailored to release more than $1\times10^{-6}$ mmol of oxygen per day over an extended time period (e.g. over 30 days). The weight ratio of the hydrophobic polymeric support structure to solid peroxide particles can range from 1:1 to 99:1 or 20:80 to 80:20 or 30:70 to 70:30. Alongside fabrication of the base microbead platform, further methods for microbead modification are detailed, including porogen inclusion and use of outer polymer layering, to provide for tailored and unique oxygen release profiles and/or co-delivery systems for release of oxygen and another agent such as a therapeutic agent.

Compositions of the present disclosure provide for a plurality of spherical microbeads that have the characteristic for extended release of one or more agents over a time frame. The extended release can be tailored as desired by designing the microbeads to release over a time frame of a week to a few weeks or 30 days or more. The agent can include solid oxygen-generating peroxide particles or a therapeutic agent (e.g., 17β-estradiol, dexamethasone, cyclosporin, fingolimod, fluticasone propionate, mometasone furoate, and other therapeutic glucocorticoids or therapeutic proteins such as CXCL12 and TGF-beta). The microbead can have an average particle diameter of about 100 to 1000 μm or with tailored ranges based on desired applications (e.g. about 100-200 μm for microscale, about 300-600 μm for macroencapsulation). The microbeads have a hydrophobic polymeric support structure that can be biocompatible. The hydrophobic polymeric support structure material can be mixed with one or more types of agents (e.g., solid oxygen-generating peroxide particles, therapeutic agents) in an amount sufficient for extended release of agent for the desired time frame. In a particular aspect, the agent can be an oxygen-generating agent and the microbead can have the characteristic of extended release of oxygen at levels of $1\times10^{-6}$ mmol of oxygen per day for about 30 days or more. The time frame can be customized to less than 14 days to over 30 days, depending on the desired application and oxygen needs of the tissue.

The hydrophobic polymeric structure can be made of a material selected from: organosilicones, poly(ethersulfone), poly(ethylene oxide terephthalate) block copolymers, polysulfone, and combinations thereof. The weight ratio of biocompatible polymeric support to agent(s) can range from 1:1 to 99:1 or about 1:1 to 10:1 or 20:80 to 80:20 or 30:70 to 70:30 depending on the intended use (e.g., concentration to be released as a function of time for a desired time frame).

The agent can be a solid oxygen-generating peroxide particle. The solid oxygen-generating particles can be $CaO_2$, MgO, SPO, or other reactive peroxides. The solid oxygen-generating peroxide particles have a diameter of about 1 to 50 μm and become encapsulated within the polymeric structure. After exposure and migration of water into the microbead structure, peroxide particles react to rapidly release gaseous oxygen into the surrounding environment.

In addition to an agent, the hydrophobic polymeric support structure material can be mixed with porogens that can be used to further modulate the release of the agents. The porogen can include salt, glucose, or hydrogels such as PEG.

The modulation of the release time frame can also be tailored by applying an outer layer on the surface of the primary spherical microbeads. The microbeads can have an outer layer that is made of a material selected from: organosilicones, poly(ethersulfone), poly(ethylene oxide terephthalate) block copolymers, polysulfone, and combinations thereof. The outer layer can have a thickness of about 5 to 25 μm. In addition, the microbeads can be tailored so that one or more types of agents (e.g., a therapeutic agent, a solid oxygen-generating peroxide particle, or a combination thereof) or porogens are included in the outer layer.

The biocompatible polymeric structure that comprises the microbead is non-degradable and hydrophobic, which provides unique control in the migration of water into the microbead structure, as well as in the release of the entrapped agent. For peroxide-based reactions, the resulting internal reaction of the housed oxygen-generating particles results in release of oxygen as well as sub-cytotoxic levels of hydrogen peroxide ($H_2O_2$) and $Ca^+$ ions.

EXAMPLE

To address challenges of other technologies, oxygen-generating microbeads were designed, which permit easy manipulation within 3D structures and greater geometric flexibility. To facilitate improved, unique oxygen-release profiles, a process of generating porosity and modular layering of polymer was developed. Inclusion of these modifications allows for reduction in burst release of oxygen and extended release period due to greater control of osmotic gradients resulting in fundamentally different and improved oxygen release dynamics.

Figure 1B:
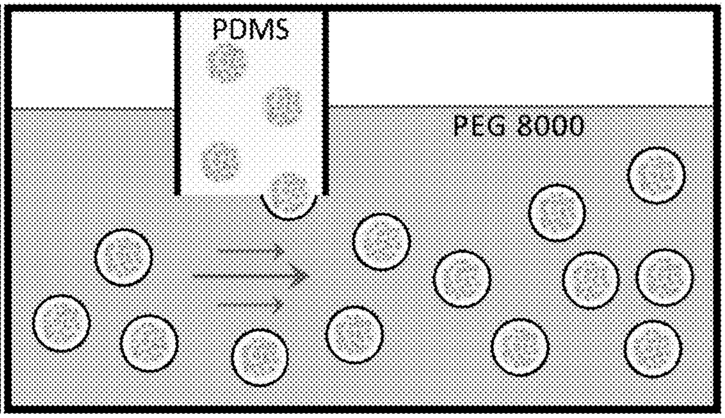

Calcium peroxide ($CaO_2$) was loaded within PDMS and homogenously distributed using a THINKY Mixer at 2000 rpm for 1 minute. If porosity within the polymeric structure was desired for the specific application, micron-scale porogens (i.e., salt particles) were also mixed into the PDMS alongside $CaO_2$ particles. The resultant mixture was fabricated into cured microbeads via emulsion in 100° C. Polyethylene glycol (PEG) 8000 liquid (FIG. 1). If further modification was desired in order to facilitate different release profiles or the co-release of another therapeutic agent, microbeads were then dried and mixed into a PDMS, PDMS-$CaO_2$, and/or PDMS-Therapeutic solution and injected into a vigorously stirred PEG 8000 liquid. After thermally curing at 100° C. for 2 hours, microbeads within the PEG media were submerged in a solution of 1% Pluronic-127 to dissolve PEG and prevent clumping of the microbeads due to hydrophobic-hydrophobic interactions. Microbeads were sorted using metal sieves to obtain the desired size range based on the application (e.g., about 100-600 micrometers in diameter). The resulting microbead size and shape were confirmed using a Scanning Electron Microscope (SEM).

To characterize release, 10-25 mg of microbeads were immersed in 1 ml PBS solution at 37° C. for a 30-day in vitro release study. The kinetic release of oxygen was recorded by an optical sensor in a sealed chamber, hydrogen peroxide was characterized by colorimetric assays. To evaluate the ability of the oxygen-generating microbeads to mitigate hypoxia-induced beta cell death and dysfunction in vitro, different bead formulations (to be referred to as microporous solid oxygen-generating peroxide particles or beads) were mixed with Min6 beta cells or primary rat islet cells and co-encapsulated within an agarose hydrogel ($3.5\times10^6$ Min6 cells or 700 IEQ rat islets per construct) and incubated under low oxygen (0.01 mM oxygen tension) for 2 to 3 days. Beta cell viability and functionality were assessed by live/dead staining, Alamar Blue, and total insulin assays. For kidney capsule studies, mouse islets (400 IEQ) were isolated from C57BL/6 and then transplanted alongside 40 fibronectin-coated oxygen-generating microbeads, with a control group having blank-PDMS microbeads. After 24 hrs, kidneys were explanted, and total insulin content was quantified using ELISA.

Figure 2A:
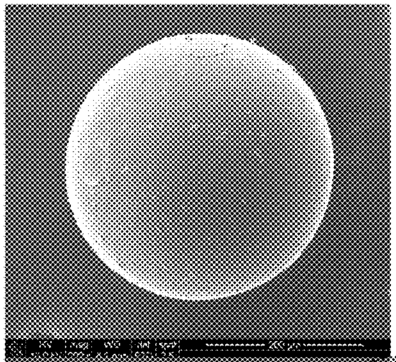
FIGS. 2A-2C illustrate SEM Images of unmodified (FIG. 2A) microporous (FIG. 2B) and layered microporous oxygen-generating microbeads (FIG. 2C).
Figure 2B:
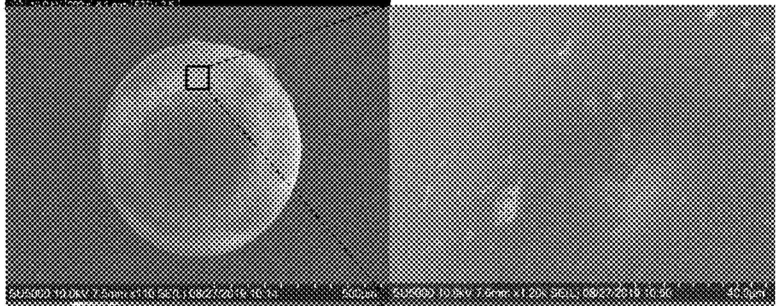
Figure 2C:
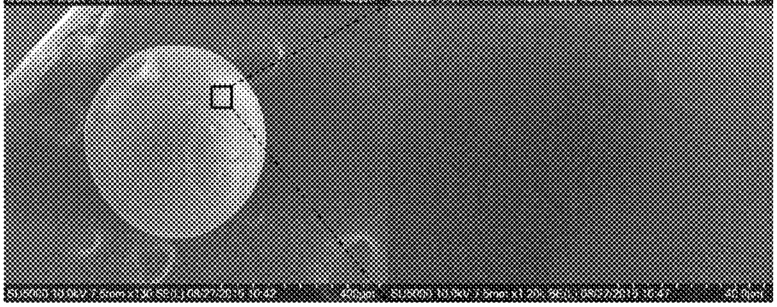
Figures 3A, 3B, 3C:
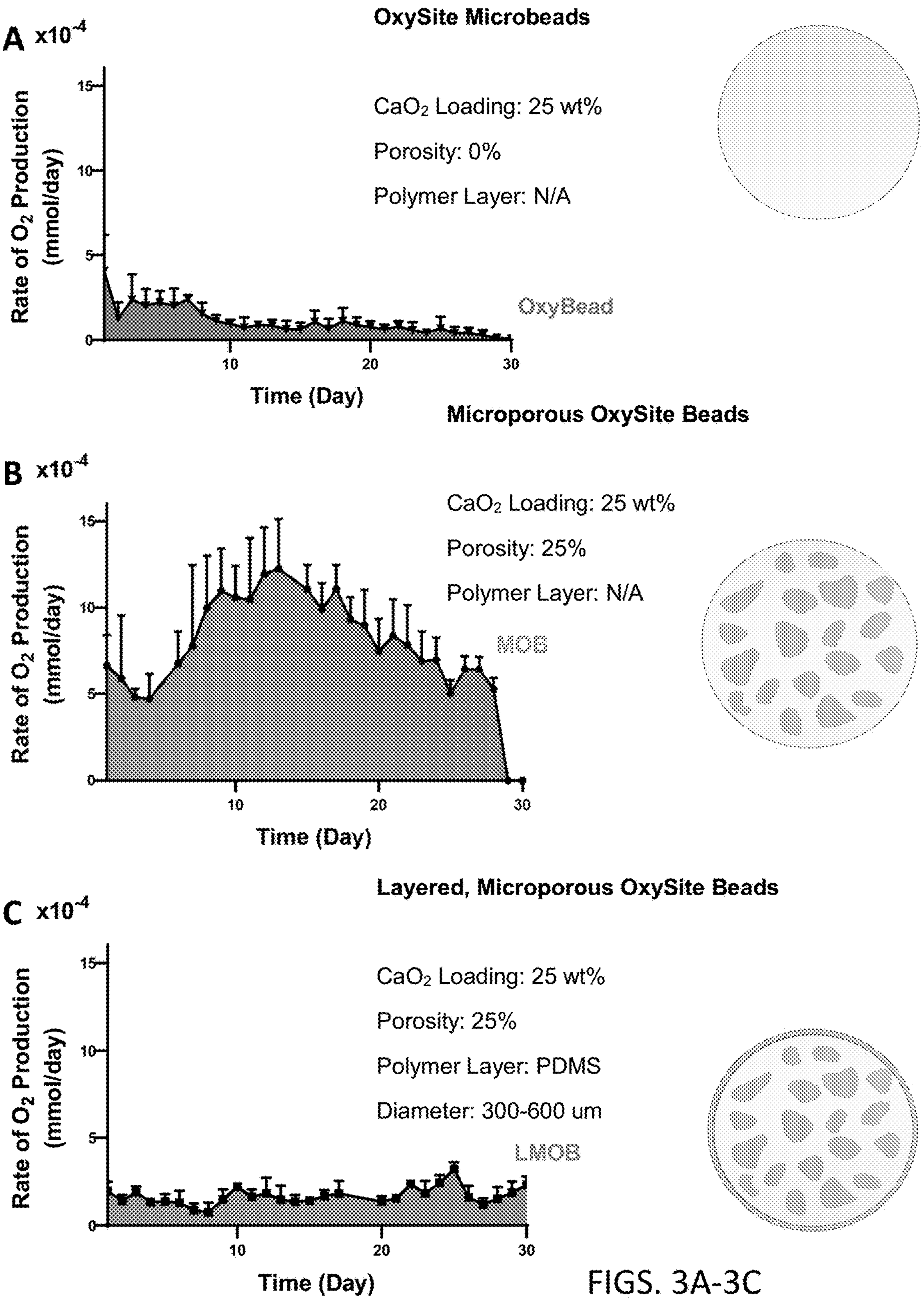
FIGS. 3A-3F illustrates modular microbead prototypes, their release profiles, and properties.
Figures 3D, 3E, 3F:
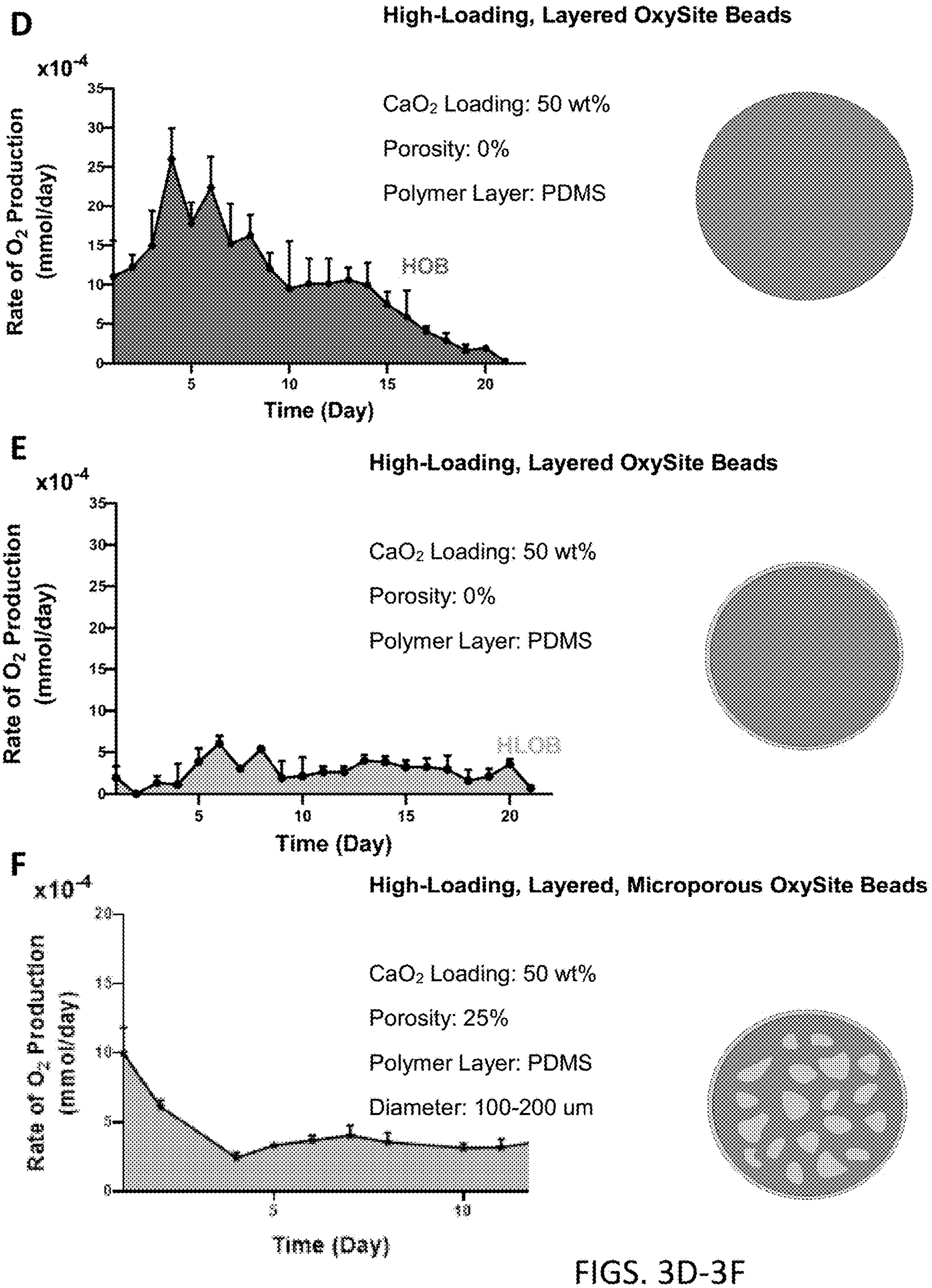
Figure 4:
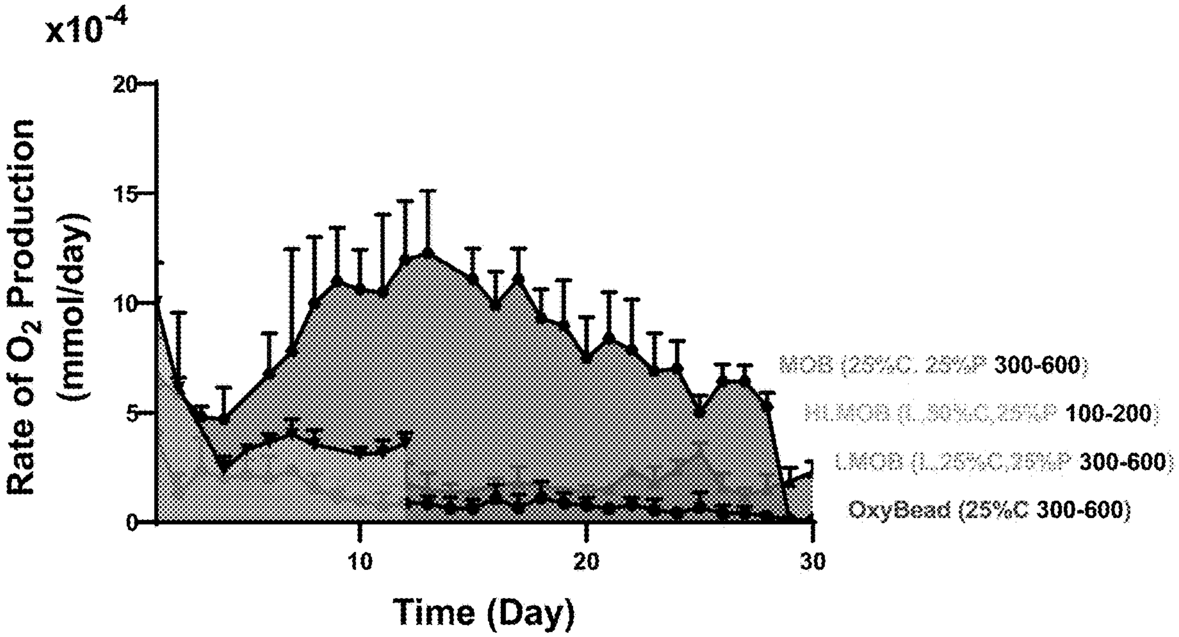
FIG. 4 illustrates an overview of release rates for microporous oxygen-generating microbeads (also referred to as "MOBs"), layered microporous solid oxygen-generating microbeads (LMOBs), and high-loading layered microporous oxygen-generating microbeads (HLMOB) compared to unmodified microporous oxygen-generating microbeads (oxybead).

Microporous solid oxygen-generating peroxide particles or microbeads were successfully fabricated into the desired size ranges of either 100-200 or 300-600 μm. SEM Images confirmed the spherical shape and size of the microbead (FIG. 2A). SEM imaging of un-layered and layered microporous solid oxygen-generating peroxide beads demonstrated creation of porosity in the beads as well as successful conformal layering of (FIG. 2B-C). The measured in vitro release profiles indicated that the solid oxygen-generating peroxide beads could generate oxygen $>8\times10^{-6}$ mmol per day for over 30 days (FIG. 3A) and layered microporous solid oxygen-generating peroxide beads could generate oxygen $>8\times10^{-4}$ mmol per day for over 30 days (FIG. 3C). Microporous beads without a layer resulted in increased oxygen production, inferring that the layering process successfully controlled osmotic pressure (FIG. 3B), allowing for more sustained release of oxygen compared to unmodified beads. Further modification through varying the $CaO_2$ loading in combination with porosity and layering resulted in distinct kinetics, demonstrating the modularity of the material and greater flexibility for alternative applications (FIG. 3D-F). Overview of release profiles for all types of oxygen-generating microbeads is presented in FIG. 4.

Figure 5:
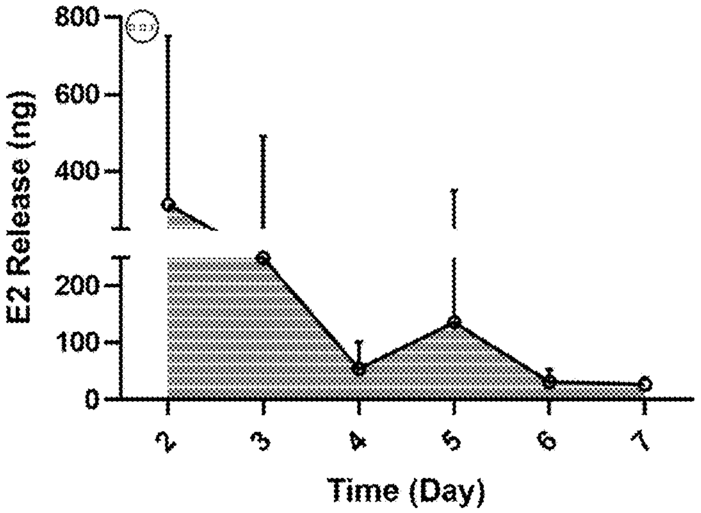
FIG. 5 illustrates the release of 17β-Estradiol (E2) from 25 mg of LMOBs layered with a 0.01 wt % solution of E2 in PDMS. O.o.r indicates values out of the assay detection range

To demonstrate the potential for the layering process to be used for release of multiple therapeutics simultaneously, microporous solid oxygen-generating peroxide beads were layered with the pro-angiogenic therapeutic 17β-Estradiol (E2) suspended in PDMS. Quantifying release in vitro demonstrated sustained release of E2 from the outer polymer layer over 7 days, showing the potential for this platform to co-deliver oxygen and other therapeutics to support the engraftment of transplanted cells in cell-based therapies (FIG. 5).

Figure 6:
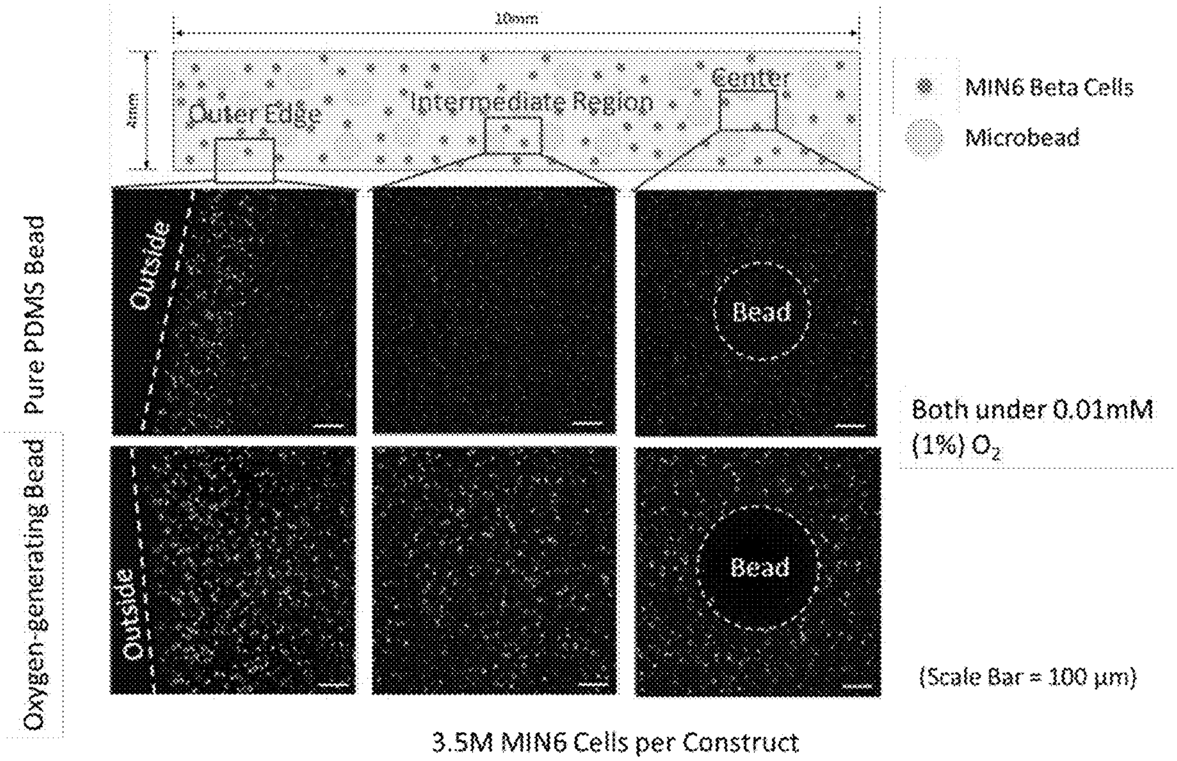
FIG. 6 illustrates live/dead imaging of microbeads and Min6 β-cells encapsulated within an agarose hydrogel. Gels were cultured over 72 hrs under hypoxic conditions before analysis
Figures 7A, 7B, 7C, 7D:
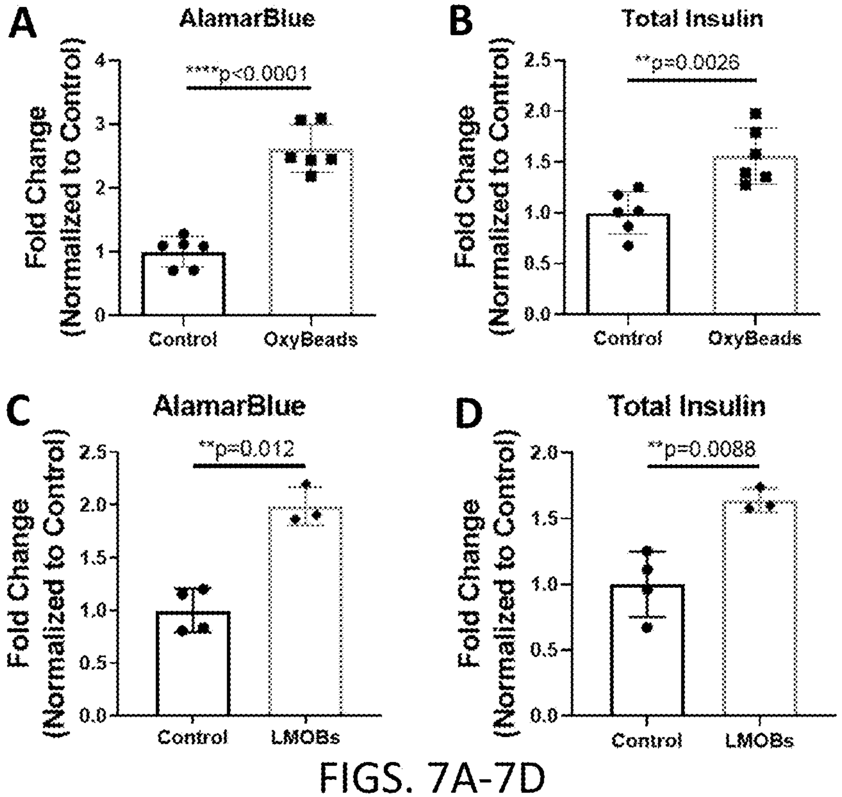
FIGS. 7A-7D illustrates AlamarBlue fluorescence and total insulin content of agarose-encapsulated Min6 after 72 hrs of hypoxic culture.
Figures 8A, 8B, 8C:
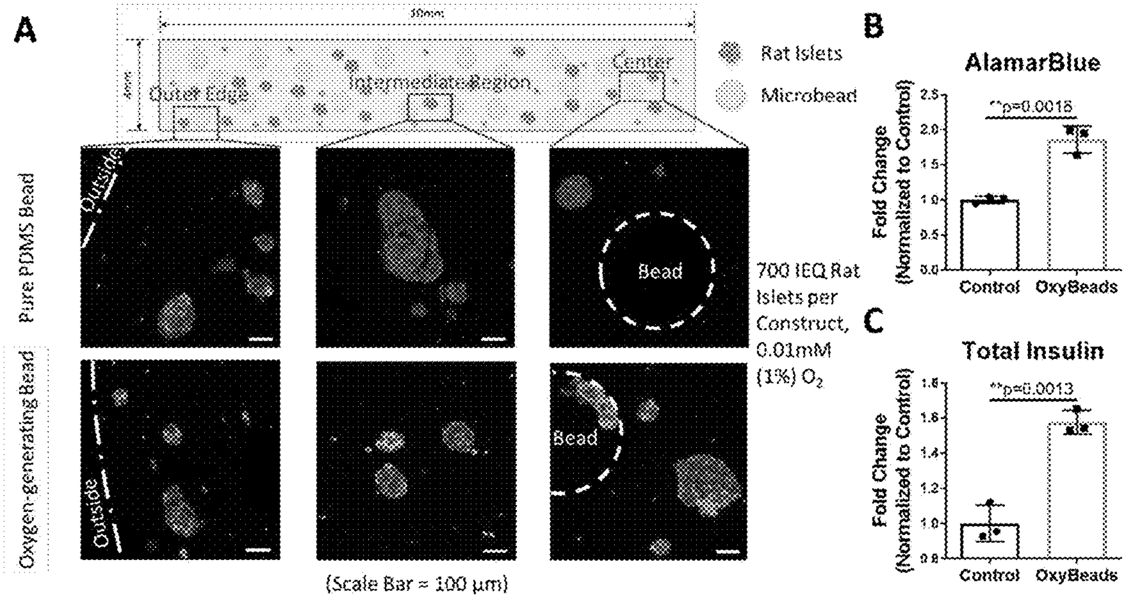
FIGS. 8A-8C illustrates live/dead imaging, AlamarBlue fluorescence, and total insulin content of agarose hydrogel containing microbeads and primary rat islet cells. Gels were cultured over 48 hrs under hypoxic conditions before analysis.
Figure 9:
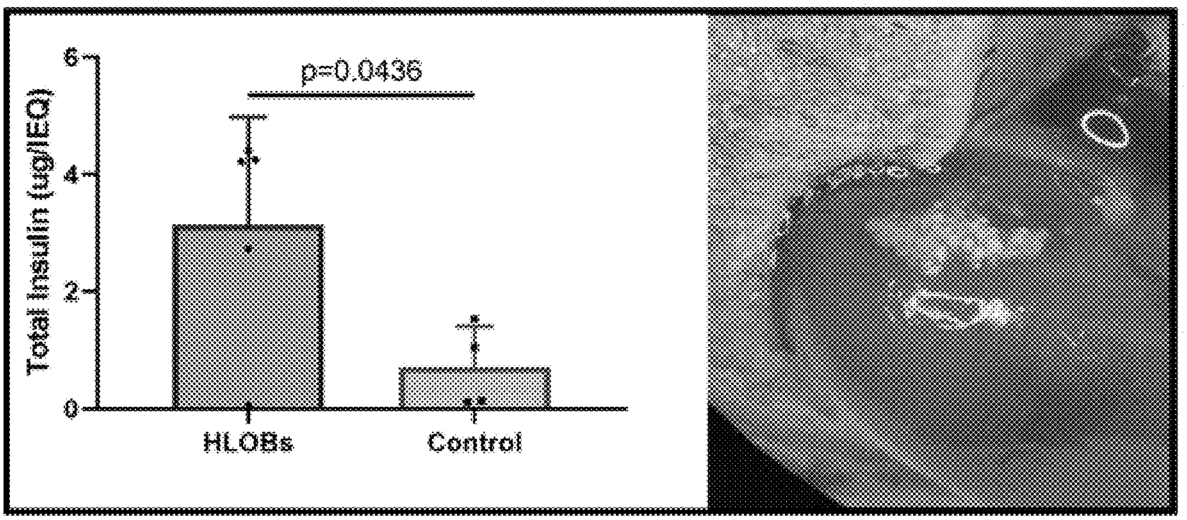
FIG. 9 illustrates total insulin content of C57BL/6 islets after transplantation in the murine kidney capsule alongside oxygen generating microbeads.

Following 3-day in vitro culture with Min6 β-cells under hypoxic conditions, live/dead whole-mount images revealed a homogenous distribution of viable cells throughout the agarose macroconstruct containing oxygen-generating microbeads (FIG. 6; bottom row). This was in stark comparison to control constructs that contained PDMS-only microbeads, which exhibited viable cells only on the outer periphery of the construct ((FIG. 6; top row). This overall loss in viability was quantified via total metabolic activity using AlamarBlue. This assay showed over a 2.5-fold increase in overall metabolic activity, when compared to control constructs (FIG. 7A) for microporous solid oxygen-generating peroxide beads and a 2-fold increase for layered microporous solid oxygen-generating peroxide beads (FIG. 7C). This indicates that bead formulations can successfully support MIN6 metabolic activity under hypoxic conditions. Further, total insulin levels for groups with microporous oxygen-generating microbeads and layered microporous oxygen-generating microbeads were over 1.5-fold higher than the control group under the same hypoxic condition (FIGS. 7B & D). Same trends were observed following 2-day in vitro culture with primary rat islet cells under hypoxic conditions, as agarose hydrogel containing oxygen-generating microbeads had more viable cells across the whole construct (FIG. 8A), 1.9-fold increased overall metabolic activity (FIG. 8B), and 1.6-fold increased total insulin content (FIG. 8C), when compared to control constructs that contained PDMS-only microbeads.

Co-transplant of C57BL/6 mouse islets alongside microbeads in a murine kidney capsule model resulted in an increase in total insulin content after 24 hours compared to islets transplanted alongside PDMS-only The microporous oxygen-generating microbead based biomaterial can be reproducibly fabricated into a microbead form within controlled size ranges depending on the desired application. This microbead platform can be further modified to produce improved, unique release profiles not previously seen with this biomaterial. These microbeads can generate oxygen for more than 30 days, with minimal cytotoxic by-products. Layering instead with therapeutics suspended in PDMS allowed for sustained release of a pro-angiogenic agent, demonstrating the potential for this platform to permit the local release of multiple therapeutics simultaneously. Compared to control PDMS-only microbeads, the co-culture of beta cells with microbeads within immunoisolatory agarose macrogels resulted in sustained and significant elevations in viability and functionality under hypoxic condition in vitro. Co-transplantation of C57BL/6 islets with these modular microbeads into the murine kidney capsule resulted in significantly higher total insulin content after 24 hrs demonstrating the potential of this platform to provide oxygen in microscale transplant environments. With these promising results and the flexibility of the microbead platform, this approach could be easily translated to numerous tissue engineering platforms.

REFERENCE LIST

1. Coronel et al., *Biomaterials,* 2019, 210; p 1-11.
2. Coronel et al., *Biomaterials,* 2017, 129; p 139-151.
3. Pedraza E, et al., *Proc Natl Acad Sci USA,* 2012, 109; p 4245-4250.

The invention claimed is:

1. A composition comprising: a plurality of spherical microbeads having the characteristic for extended release of oxygen for a first time frame, wherein the plurality of microbeads has an average particle diameter of about 100 to 1000 μm, wherein the microbeads have a hydrophobic polymeric support structure containing solid oxygen-generating peroxide particles in an amount sufficient for extended release of oxygen, wherein the microbeads have an outer layer that is made of a material selected from: organosilicones, poly(ethersulfone), poly(ethylene oxide terephthalate) block copolymers, polysulfone, and combinations thereof.

2. The composition of claim 1, wherein the microbeads each have the characteristic of extended release of oxygen for about 30 days or more.

3. The composition of claim 1, wherein the microbeads each have the characteristic of extended release of oxygen for about 1 week or more.

4. The composition of claim 1, wherein the hydrophobic polymeric support structure is made of a material selected from: organosilicones, poly(ethersulfone), poly(ethylene oxide terephthalate) block copolymers, polysulfone, and combinations thereof.

5. The composition of claim 1, wherein the solid oxygen-generating peroxide particles is a $CaO_2$ particle.

6. The composition of claim 1, wherein the solid oxygen-generating peroxide particles have a diameter of about 1 to 50 μm.

7. The composition of claim 1, wherein the microbeads have a weight ratio of hydrophobic polymeric support structure material to solid oxygen-generating peroxide particles of about 1:1 to 99:1.

8. The composition of claim 1, wherein the microbeads have porogens within the microbead.

9. The composition of claim 1, wherein the microbeads have a therapeutic agent within pores, wherein the microbeads have a characteristic for extended release of the therapeutic agent for a second time frame.

10. The composition of claim 9, wherein the microbeads each have the characteristic of extended release of the therapeutic agent for about 30 days or more.

11. The composition of claim 9, wherein the microbeads each have the characteristic of extended release of the therapeutic agent for about 3 days or more.

12. A composition comprising: a plurality of spherical microbeads, wherein the plurality of microbeads has an average particle diameter of about 100 to 1000 μm, wherein the microbeads have a hydrophobic polymeric support structure containing solid oxygen-generating peroxide particles in an amount sufficient for extended release of oxygen, wherein the microbeads each have the characteristic of extended release of oxygen at levels of $1\times10^{-6}$ mmol of oxygen per day or more for about 30 days or more, wherein the microbeads have porogens within the microbead, wherein the porogens are selected from salt, glucose, or hydrogels or a combination thereof, wherein the microbeads have a therapeutic agent within the pores, wherein the microbeads each have the characteristic of extended release of the therapeutic agent for about 30 days or more.

13. The composition of claim 12, wherein the hydrophobic polymeric support structure is made of a material selected from: organosilicones, poly(ethersulfone), poly (ethylene oxide terephthalate) block copolymers, polysulfone, and combinations thereof, wherein the solid oxygen-generating peroxide particles is a $CaO_2$ particle.

14. A composition comprising: a plurality of spherical microbeads having the characteristic for extended release of oxygen for a first time frame, wherein the plurality of microbeads has an average particle diameter of about 100 to 1000 μm, wherein the microbeads have a hydrophobic polymeric support structure containing solid oxygen-generating peroxide particles in an amount sufficient for extended release of oxygen, wherein the microbeads have an outer layer that is made of a material selected from: organosilicones, poly(ethersulfone), poly(ethylene oxide terephthalate) block copolymers, polysulfone, and combinations thereof, the wherein outer layer has a thickness of about 11 to 25 μm, and wherein the outer layer includes a therapeutic agent, a solid oxygen-generating peroxide particle, or a combination thereof.

15. The composition of claim 14, wherein the microbeads have porogens within the microbead, wherein the porogens are selected from salt, glucose, or hydrogels or a combination thereof, wherein the microbeads have a therapeutic agent within the pores.

16. The composition of claim 15, wherein the microbeads each have the characteristic of extended release of the therapeutic agent for about 3 days or more.

17. The composition of claim 16, wherein the hydrophobic polymeric support structure is made of a material selected from: organosilicones, poly(ethersulfone), poly (ethylene oxide terephthalate) block copolymers, polysulfone, and combinations thereof, wherein the solid oxygen-generating peroxide particles is a $CaO_2$ particle.

18. The composition of claim 1, wherein the outer layer has a thickness of about 11 to 25 μm.

19. The composition of claim 1, wherein the outer layer includes a therapeutic agent, a solid oxygen-generating peroxide particle, or a combination thereof.

20. A composition comprising: a plurality of spherical microbeads having the characteristic for extended release of oxygen for a first time frame, wherein the plurality of microbeads has an average particle diameter of about 100 to 1000 μm, wherein the microbeads have a hydrophobic polymeric support structure containing solid oxygen-generating peroxide particles in an amount sufficient for extended release of oxygen, wherein the microbeads have porogens within the microbead.

21. The composition of claim 20, wherein the porogens are selected from salt, glucose, or hydrogels or a combination thereof.

* * * * *